United States Patent
Gleich et al.

(10) Patent No.: US 7,370,656 B2
(45) Date of Patent: May 13, 2008

(54) METHOD AND ARRANGEMENT FOR INFLUENCING MAGNETIC PARTICLES AND DETECTING INTERFERING MATERIAL

(75) Inventors: Bernhard Gleich, Hamburg (DE); Jürgen Weizenecker, Norderstedt (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 99 days.

(21) Appl. No.: 10/552,801

(22) PCT Filed: Apr. 5, 2004

(86) PCT No.: PCT/IB2004/001119

§ 371 (c)(1),
(2), (4) Date: Oct. 11, 2005

(87) PCT Pub. No.: WO2004/091392

PCT Pub. Date: Oct. 28, 2004

(65) Prior Publication Data

US 2007/0007486 A1    Jan. 11, 2007

(30) Foreign Application Priority Data

Apr. 15, 2003    (EP)    ................................ 03101012

(51) Int. Cl.
A61B 19/00    (2006.01)
A61N 1/00    (2006.01)
(52) U.S. Cl. .......................................... 128/899; 600/9
(58) Field of Classification Search ................ 128/899; 606/27–31; 607/103; 600/9–15; 219/634
See application file for complete search history.

(56) References Cited

U.S. PATENT DOCUMENTS

| 4,819,642 | A | 4/1989 | Andersen et al. |
| 6,082,366 | A | 7/2000 | Andra et al. |
| 6,470,220 | B1 * | 10/2002 | Kraus et al. ................ 607/103 |
| 6,541,966 | B1 | 4/2003 | Keene |
| 2001/0011151 | A1 | 8/2001 | Feucht |
| 2001/0012915 | A1 | 8/2001 | Aurin et al. |

FOREIGN PATENT DOCUMENTS

| DE | 3813479 A1 | 11/1988 |
| DE | 10151778 A1 | 5/2003 |
| EP | 0913167 A2 | 5/1999 |
| WO | 2004018039 A1 | 3/2004 |

OTHER PUBLICATIONS

ISR: PCT/IB04/001119, Aug. 23, 2004.
Written Opinion: PCT/IB04/001119, Aug. 23, 2004.

* cited by examiner

Primary Examiner—John P Lacyk

(57) ABSTRACT

The invention relates to a method and an arrangement for influencing magnetic particles in a region of action. Methods and arrangements of this kind can be used to determine the spatial distribution of magnetic particles in the region of action or to heat up the magnetic particles locally. If, in addition to the magnetic particles, there is also interfering material in the region of action then this material may heat up in an unwanted way. To avoid unwanted heating-up of this kind, any interfering material that may be present is detected beforehand. If there is interfering material present, then an examination or investigation, or treatment, can be carried out with changed system parameters.

13 Claims, 5 Drawing Sheets

METHOD AND ARRANGEMENT FOR INFLUENCING MAGNETIC PARTICLES AND DETECTING INTERFERING MATERIAL

The invention relates to a method and an arrangement for influencing magnetic particles in a region of action.

Magnetic particles are relatively easy to detect and can therefore be used for examinations and investigations (particularly medical ones). An apparatus and method of this kind for determining the spatial distribution of magnetic particles in an examination zone (i.e. a region of action), and the use therein of suitable magnetic particles, are described in as yet unpublished German patent application DE10151778.5 (applicant's reference PHDE010289). This patent application will be referred to below as D1. To allow the spatial distribution of magnetic particles in an examination zone to be determined, a spatially inhomogeneous magnetic field is generated that has at least one zone in which the magnetization of the particles is in a state of non-saturation. Changing the position of this zone within the examination zone produces a change in magnetization that can be detected from the outside and that gives information on the spatial distribution of the magnetic particles in the examination zone.

Magnetic particles can also be used to heat their surroundings, particularly in medical hyperthermia. A method and a system of this kind for the local heating of regions of an object by variation of the magnetization of magnetic or magnetizable substances is described in as yet unpublished German patent application DE10238853.9 (applicant's reference PHDE020195). This patent application will be referred to below as D2. To heat the target region (i.e. the region of action) locally, an inhomogeneous magnetic field is generated having a pattern in space of its magnetic field strength such that a first sub-zone having a low magnetic field strength (the magnetic particles are not saturated in it) and a second sub-zone having a higher magnetic field strength are generated in the target region. The position in space of the two sub-zones in the target region is then changed for so long at a given frequency that the particles heat up to a desired temperature due to a frequent change in magnetization.

However, unwanted heating-up may possibly occur with the methods disclosed in D1 and D2.

It is therefore an object of the invention to develop a method by which it is possible for heating-up of this kind to be reduced or avoided, and to develop an apparatus with which this method can be performed.

This object is achieved by a method for influencing, in a region of action, magnetic particles that have been introduced into an object, which method has the following steps:
a) detection of interfering material in or on the object,
b) generation of a magnetic field having a pattern in space of its magnetic field strength such that a first sub-zone (301) having a low magnetic field strength and a second sub-zone (302) having a higher magnetic field strength are formed in the region of action,
c) changing the position in space of the two sub-zones in the region of action so that the magnetization of the particles changes locally,
d) if required, acquiring signals that depend on the magnetization in the region of action, which magnetization is influenced by the above change in position.

The invention is based on the finding that, in performing the methods disclosed in D1 and D2, heating-up can be observed of items made of interfering material that are situated in or on the object being examined, investigated or treated. The heating-up may be so severe in this case that the object is damaged. Within the meaning of the invention, interfering material is ferromagnetic material and material having good conductivity for electrical current, and particularly metal or alloys thereof. If the object is a patient, then dental fillings of amalgam, artificial joints, rods or screws fitted in or on bones, or even items situated on the outside of the patient's body such as personal adornments (ear-rings, adornments in piercings) heat up. A planned examination or investigation or planned treatment by the methods disclosed in D1 and D2 may still be performed under certain circumstances if any possible heating-up during the examination, investigation or treatment is precluded by, for example, changing the system parameters, or if the interfering material is removed beforehand.

In a first step of the method according to the invention, any interfering material that may be present is detected. There are different possible ways of doing this. If interfering material is brought into the zone of influence of an inductive means, such as a coil, for example, there is a change in the resulting overall magnetic field. This is equivalent to a change in the measured inductance of the inductive means when the interfering material is brought into its zone of influence. This effect is made use of in the manner claimed in claim 2 to determine the presence of interfering material. On the one hand, known detectors may be used for this purpose. If one of the means used for influencing the magnetic particles is an inductive means, then, on the other hand, this inductive means may be used as a detector, as claimed in claim 3. This saves on components for the apparatus and an apparatus for performing the method can be produced more economically.

Alternatively, the detection of interfering material may be performed as claimed in claim 4. For detection, steps of the method are performed that are similar to the steps that take place in the treatment, examination or investigation proper. It is, however, essential for care to be taken to see that the material does not heat up in a non-allowable way even during the detection itself. This can be achieved on the one hand by employing reduced spatial resolution, given that the measures by which spatial resolution is reduced also produce a reduction in the heating-up of interfering material. As can be seen from documents D1 and D2, spatial resolution may, for example, be reduced by reducing the strength of the magnetic field by which the two sub-zones are produced. So that the position in space of the two sub-zones cannot be changed in such a way as to leave the region of action, the amplitude of the field strength of the temporally variable magnetic fields by which the position in space of the two sub-zones is changed is reduced at the same time, which likewise and to an additional degree reduces the heating-up. Another measure for reducing spatial resolution is to use a coarser scanning grid during the changing of the position in space of the sub-zones. On the other hand, non-allowable heating up during the detection may also be precluded by performing the change in the position in space of the two sub-zones more slowly than in the examination or treatment.

The measures just mentioned have another beneficial effect: static and dynamic forces that the magnetic fields exert on the interfering material are also reduced. This is of interest if, for example, the object is a patient in whom there is a piece of shrapnel from a bomb and who, as a result of an excessively high field strength for the magnetic fields and of the forces resulting therefrom, might move onto the piece of shrapnel.

The method claimed in claim 5 is used particularly to detect ferromagnetic material. Since, in the detection, there are no magnetic particles contained in the object, the signals detected originate solely from the interfering material.

With the method claimed in claim 6, it is possible for the actual examination or treatment of the object to be performed immediately following the detection of the interfering material, thus producing a more efficient sequence for the method. If there are both magnetic particles and interfering material present in the object, then, as claimed in claim 7, it is seen from an examination of the spectrum of the signal acquired that the spectrum contains spectral components which derive from the magnetic particles and also spectral components which derive from the interfering material.

To obtain evidence of interfering material, the known spectral components for the magnetic particles are, for example, subtracted from the overall spectrum of the signal acquired, thus leaving the spectral components for the interfering material and enabling the conclusion to be drawn that the latter is at least present.

If interfering material has been detected, then it should be removed if at all possible. If this is not possible, then, to protect the object, a planned examination or planned treatment may have to be abandoned if necessary. If an examination or treatment is still to be performed in spite of the fact that interfering material is present in the vicinity of the region of action, the risk of non-allowable heating-up can be avoided by taking suitable measures. The interfering material may, for example, be actively screened off with a local opposing magnetic field or may be passively screened off (such as with metal screening plates). In this way, the influence of the temporally variable magnetic fields on the interfering material is reduced to such a degree that the interfering material does not heat up or does not interfere with the treatment or examination. As an alternative or in addition, the method claimed in claim 8 may be performed, by, for example, reducing the frequency of the temporally variable magnetic fields used. This can be done automatically by an arrangement suitable for performing the method.

Excessive heating-up can also be avoided with the method claimed in claim 9. The lower spatial resolution may, for example, be obtained by reducing the strength of the magnetic field or by causing the change in the position in space of the two sub-zones to take place in a coarser scanning grid. This can also be done automatically by an appropriate change in system parameters. As a result of the lower strengths of the magnetic fields used and of the slowed pattern they follow with time, the interfering material is influenced to such a small degree that any excessive heating-up is ruled out.

As well as the possible heating-up of interfering material, there is another unwanted effect that has shown up in other examinations: if interfering material finds its way into the zone of influence of an external magnetic field, then an opposing magnetic field forms in and/or around the interfering material, as a result of eddy currents or magnetization, for example, which opposing magnetic field superimposes itself on the external magnetic field to form an overall magnetic field. The field-line pattern of this overall magnetic field is different from that of the external magnetic field, as a result of which the position in space of the two sub-zones changes or in other words shifts or is displaced uncontrollably. However, for the magnetic particles to be influenced in a targeted fashion, it is necessary for the exact position of the sub-zones to be known. This knowledge that is needed of the current positions in space of the two sub-zones is thus only limited or does not exist at all, which has an adverse effect on the accuracy and success of the treatment or examination. The detection of the interfering material thus not only enables action to be taken in response to unwanted heating-up but also allows a user to be directed to a possible inaccuracy in the system.

As claimed in claim 10, the object is also achieved with an arrangement for influencing magnetic particles in a region of action, which arrangement has:
a) means for detecting interfering material,
b) means for generating a magnetic field having a pattern in space of its magnetic field strength such that a first sub-zone (301) having a low magnetic field strength and a second sub-zone (302) having a higher magnetic field strength are formed in the region of action,
c) means for changing the position in space of the two sub-zones in the region of action,
d) if required, means for acquiring signals, which signals depend on the magnetization in the region of action that is influenced by the change in the position in space of the sub-zones.

The methods described above can be performed by the embodiments of this arrangement that are claimed in claims 11, 12 and 13.

These and other aspects of the invention are apparent from and will be elucidated with reference to the embodiments described hereinafter.

Figure 4:
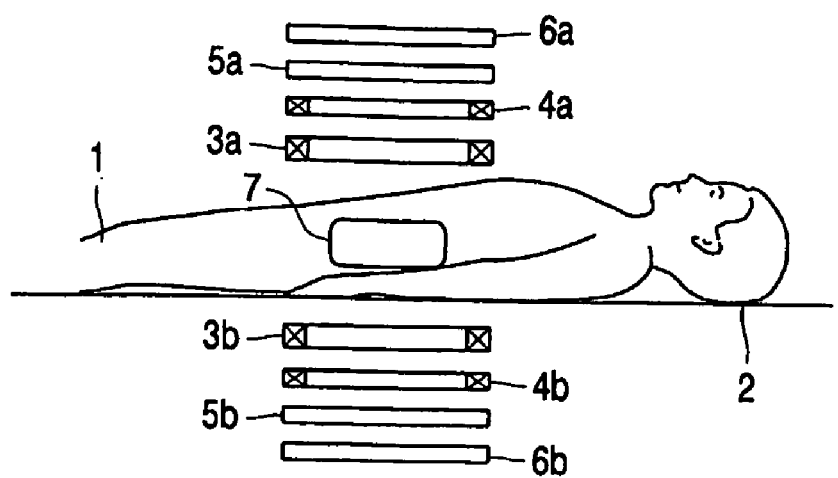
FIG. 4 shows an apparatus for performing the method according to the invention.
Figure 5:
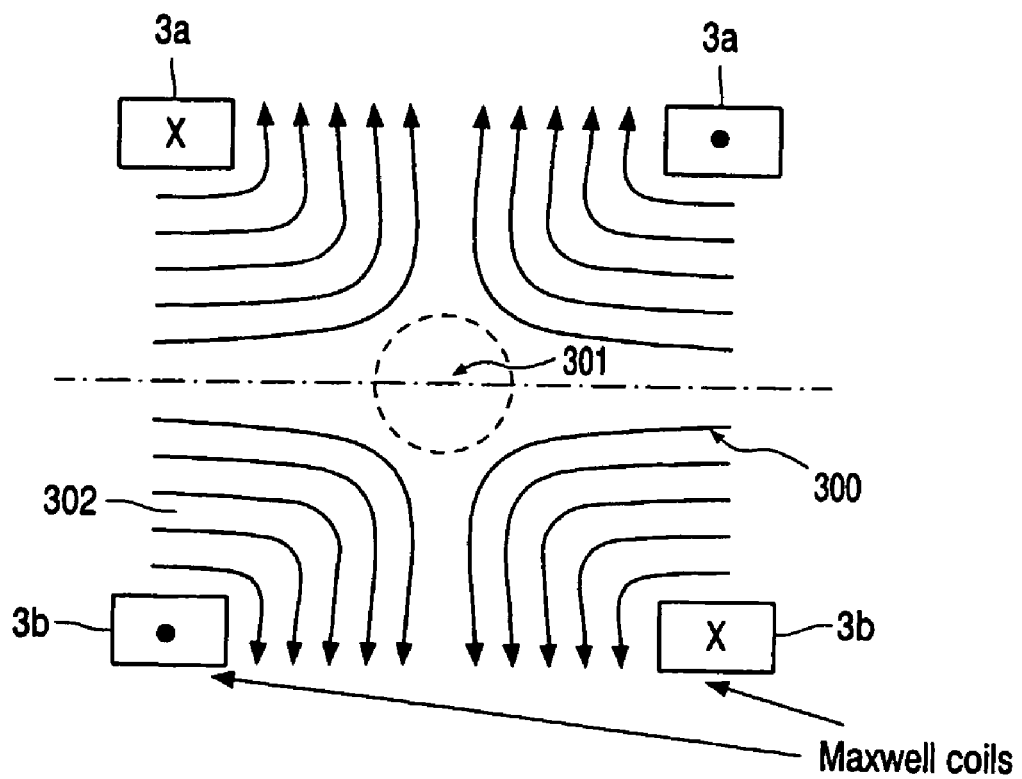
FIG. 5 shows the pattern of field lines generated by the coils contained in the apparatus.

An apparatus for performing the method according to the invention is shown in FIG. 4. In the Figure, reference numeral 1 refers to the object for examination or investigation, a patient in this case, who is situated on a patent presentation table of which only the plate 2 is indicated. Situated above and below the patient 1 and the plate 2 of the table, there are also a plurality of pairs of coils, whose region of action defines the examination zone. A first pair of coils 3 comprises the two windings 3a and 3b of identical construction that are arranged co-axially above and below the patient and through which currents of equal size but opposite directions of circulation flow. The gradiented magnetic field generated by them is shown in FIG. 5 by means of the field lines 300. Its gradient in the direction of the vertical axis of the pair of coils is almost constant and at one point along this axis it reaches a value of zero. Starting from this field-free point, the strength of the magnetic fields increases in all three directions in space with increasing distance from the point. In a zone 301 (the first sub-zone) around the field-free point, which zone is indicated by a dashed line, the field strength is so low that the magnetization of magnetic particles situated in it is not saturated, whereas outside the zone 301 it is in a state of saturation. In the remaining zone outside 301 (the second sub-zone 302), the magnetization of the particles is in a state of saturation.

If a further magnetic field is superimposed on the gradiented magnetic field in the region of action, then the zone 301 shifts in the direction of this further magnetic field, the size of the shift increasing with the strength of the magnetic field. If the magnetic field superimposed is temporally variable, then the position of zone 301 changes with time and in space accordingly. There are three further pairs of coils 4, 5 and 6, having windings 4a and 4b, 5a and 5b and 6a and 6b, to generate these temporally variable magnetic fields for any desired direction in space. For the arrangement and workings of these pairs of coils and the way in which they are operated, reference should be made to documents D1 and D2.

Finally, there is also shown in FIG. 4 a further coil 7, the purpose of which is to detect signals generated in the examination zone. In principle, any of the pairs of field-generating coils 3 to 6 could be used for this purpose. There are, however, advantages in using a separate receiving coil. A better signal-to-noise ratio is obtained (particularly if a plurality of receiving coils are used), and the coil can be so arranged and switched that it is decoupled from other coils.

Figure 6:
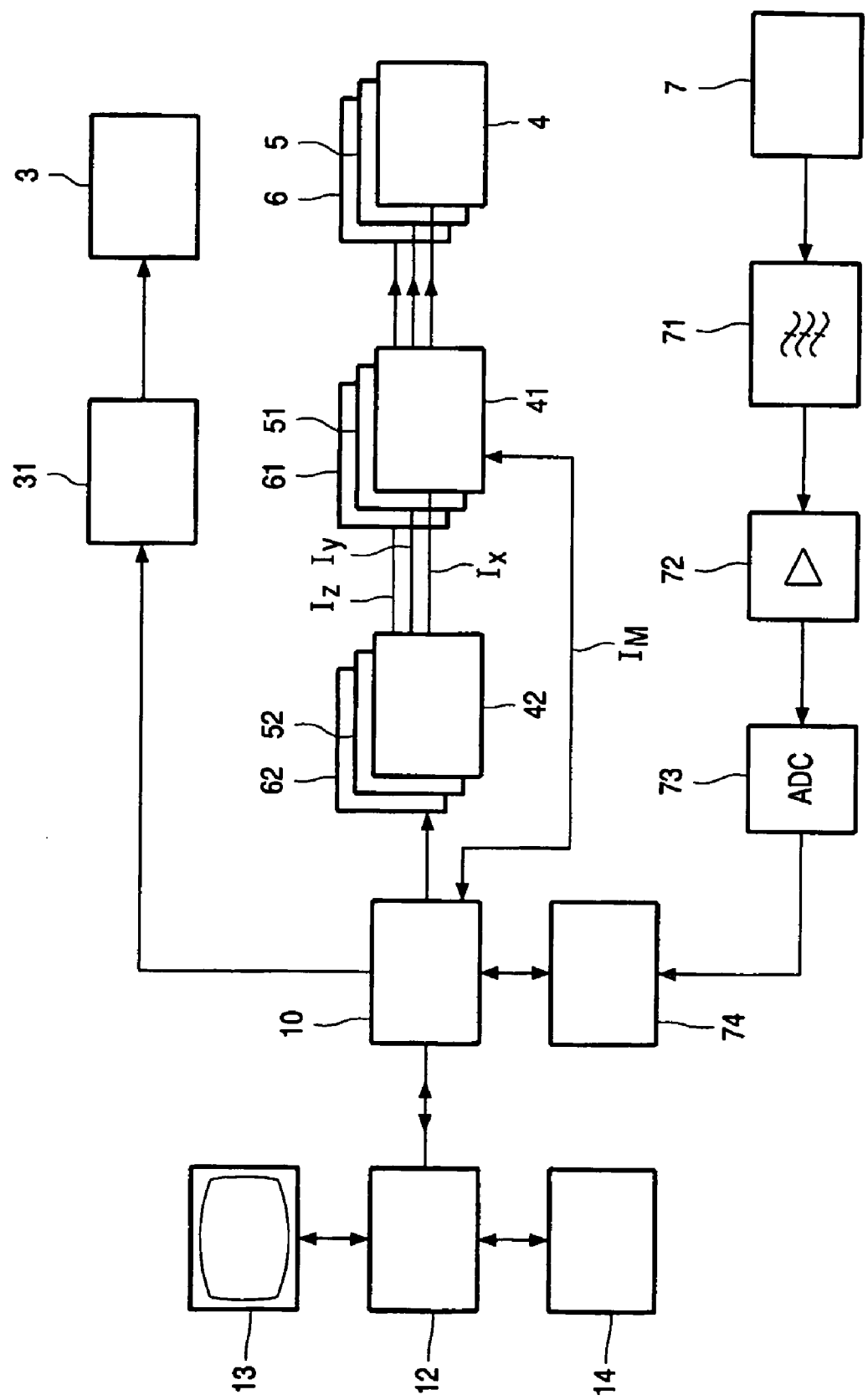
FIG. 6 is a block circuit diagram of the arrangement shown in FIG. 4.

FIG. 6 shows a block circuit diagram of the apparatus shown in FIG. 4. The diagrammatically indicated pair of coils 3 (the suffixes a and b have been omitted from all the pairs of coils in FIG. 6 for the sake of simplicity) are supplied by a controllable current source 31 with d.c. current that can be controlled—and switched on and off—by a control unit 10. The control unit 10 cooperates with a workstation 12 that is provided with a monitor 13 for showing images representing the distribution of the particles in the region of action. Inputs can be made by a user via a keyboard or some other inputting unit 14.

The pairs of coils 4, 5, 6 receive their currents from current amplifiers 41, 51 and 61. The waveforms over time of the currents Ix, Iy and Iz to be amplified, which currents generate the desired magnetic fields, are preset by respective waveform generators 42, 52 and 62. The waveform generators 42, 52, 62 are controlled by the control unit 10, which calculate the waveform over time required for the particular examination, investigation or treatment procedure and loads it into the waveform generators. In the course of the examination, investigation or treatment, these signals are read out from the waveform generators and fed to the amplifiers 41, 51, 61, which generate the currents required for the pairs of coils 4, 5 and 6 from them.

Generally speaking, a non-linear relationship exists between the shift of the zone 301 from its position at the center of the gradient coil arrangement 3 and the current through the gradient coil arrangement. Moreover, all three coils must generally generate a magnetic field if the zone 301 is to be shifted along a straight line extending off the center. Where the waveform of the currents with time is preset, this is allowed for by the control unit, with the help of suitable tables, for example. The zone 301 can therefore be shifted through the region of action along paths of any desired shape.

The signals that are received by the coil 7 that is used when the object is being examined or investigated are fed to an amplifier 72 via a suitable filter 71. The output signals from the amplifier 72 are digitized by an analog-to-digital converter 73 and fed to an image-processing unit 74, which reconstructs the spatial distribution of the particles from the signals and from the position that the zone 301 is occupying at the time during the reception of the signals. The reader is referred at this point to D1 for an exact description of the reconstruction from the signals received by coil 7. From the reconstructed signals, an image is generated that is shown on the monitor 13 of the workstation 12.

As an alternative to examination or investigation, the apparatus can also be used for the local heating of the region of action. In a similar way to the imaging, a shift of the zone 301 is produced for this purpose with the help of pairs of coils 4, 5 and 6, with the control unit 10 controlling the waveform generators 42, 52, 62 in the appropriate way. For a detailed description of the shifting of the zone 301 for the purpose of determining the spatial distribution of magnetic particles (and, furthermore, for the reconstruction of image data) or for the purpose of local heating of the region of action, reference should be made to documents D1 and D2.

Figure 1:
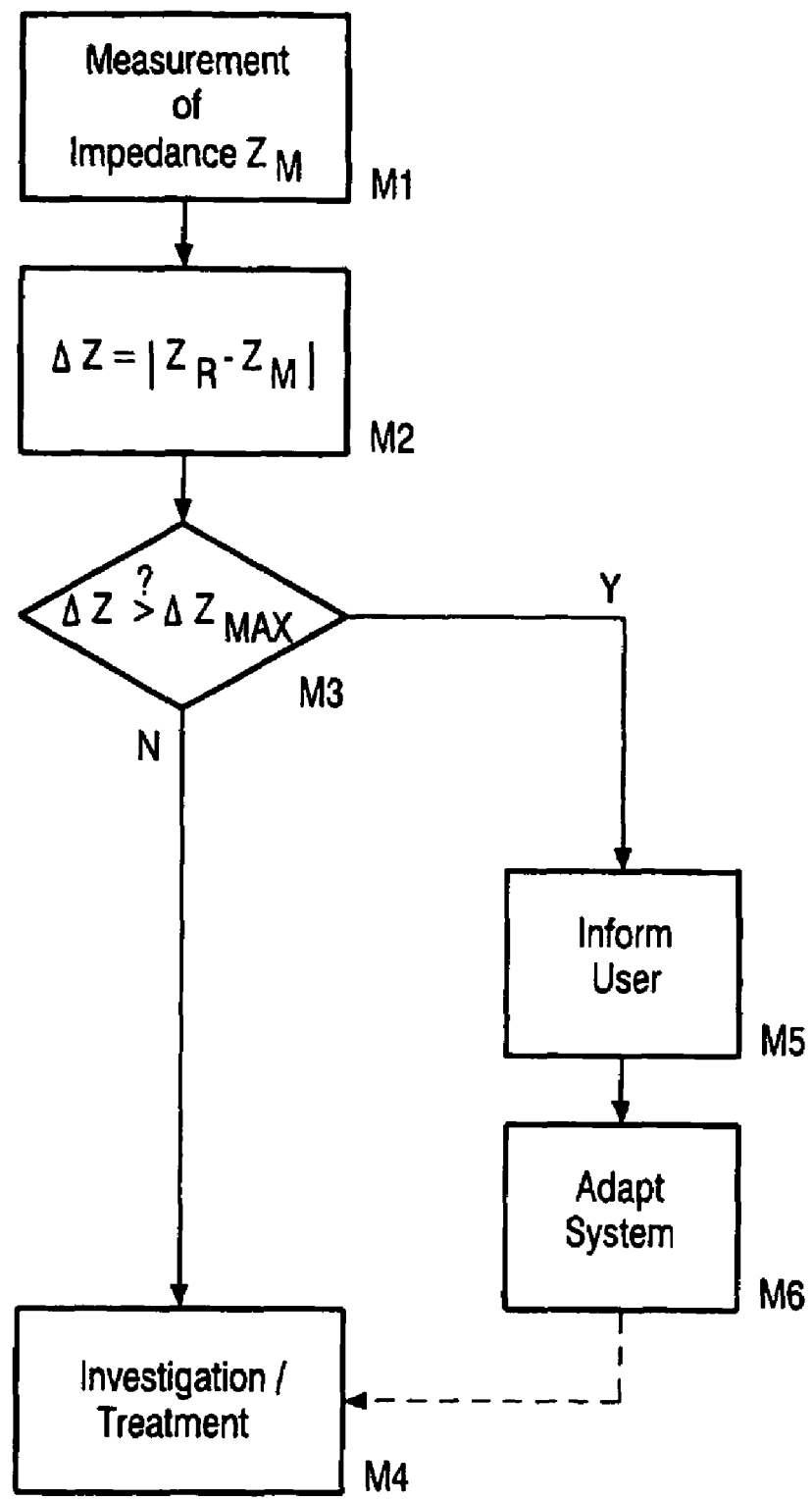
FIG. 1 is a flowchart for a first embodiment of the invention.

FIG. 1 shows the flowchart for a first embodiment of the method according to the invention. It is assumed that the patient 1 has a dental filling of amalgam and is to be examined in the neck region. Under normal circumstances, the jaw region of the patient 1 will be situated in or in the immediate vicinity of the region of action during the examination, which means that the dental filling will be influenced by the temporally variable magnetic fields from the pairs of coils 4, 5 and 6. If an examination were being performed, this would cause eddy currents to be set up in the dental filling, as a result of which the filling would heat up and lasting damage might be done to the jaw region of the patient 1.

Therefore, before the actual examination or treatment of the patient 1, the inductance of one of the inductive means belonging to the apparatus shown in FIG. 4 is determined in step M1. The inductive means is assumed to be the coil 4a, but it could equally well be any of the other coils shown. Generally speaking, the (measured) inductance of a coil is known to depend on geometrical parameters and on the characteristics of the matter in the space within the coil or of the material situated therein. It is also known that, when a coil is supplied with electrical energy, the size of the inductance of the coil has an effect on the waveform of the current or voltage. These interrelationships will not be gone into in detail here because they are part of the general knowledge of the man skilled in the art. Hence, the inductance of the coil 4a may, for example, be determined by applying a voltage pulse of square-wave form to the coil and analyzing the waveform over time of the resulting current. Another alternative for determining the inductance is to generate an alternating magnetic field with another coil of the apparatus shown in FIG. 4, such as coil 4b, for example, which field will induce a current in coil 4a by reference to which statements can be made regarding the measured inductance of coil 4a.

If, generally speaking, a coil is incorporated in an oscillating circuit, the parameters of the circuit are known to change if the inductance of the coil changes. With this alternative, which is made use of in the apparatus being elucidated here, the coil 4a is connected to an oscillating circuit whose impedance can be determined as a function of frequency. If the impedance of the oscillating circuit changes without there being any change to the other components of the oscillating circuit, then the inductance of the coil has changed. This method is also known from the prior art, and for that reason any description of further details will be dispensed with. Apart from the coil 4a, the other components of the oscillating circuit are housed in the waveform generator 42, together with a measuring means for measuring the impedance $Z_M$. To allow interfering material to be detected, the measurement of impedance is activated via the workstation 12 by means of the user control element 14. Via the control unit 10, the workstation 12 causes the waveform generator 41 to automatically determine the frequency-dependent impedance $Z_M$ of the oscillating circuit and to transmit this value to the control unit 10. For this purpose, the control unit 10 is coupled to the waveform generator 41 via a separate bi-directional link $I_M$. The impedance $Z_M$ measured is passed on by the control unit 10 to the workstation 12.

In the next step M2, the impedance $Z_M$ measured, which is generally a complex value, is compared with a reference impedance $Z_R$, which is usually complex likewise, and a (complex) difference in impedance $\Delta Z$ is determined. Depending on the computing power of the workstation 12, this can be done at many or all frequencies. To reduce the computing work, this complex comparison may, however, also take place at only a few selected frequencies at which a large change may typically be expected. The reference impedance $Z_R$ in this case is that impedance of the oscillating circuit that is measured when there are no objects or other relevant items in the region of action.

In step M3, the difference in impedance $\Delta Z$ that has been determined is compared with a maximum permitted difference in impedance $\Delta Z_{MAX}$. This maximum permitted difference in impedance $\Delta Z_{MAX}$ arises from the fact that the impedance of the oscillating circuit will be changed (though by only a minimal amount) even by objects having no interfering material being introduced into the region of action. For patients, for example, a value can be determined for the difference in impedance $\Delta Z_{MAX}$ that is the result of measurements made on a number of different patients, there being a patient having no interfering material and no magnetic materials situated in the region of action at the time of each measurement.

If the different in impedance $\Delta Z$ determined is less than the maximum permitted difference in impedance $\Delta Z_{MAX}$, then no interfering material has been detected and subsequent treatment or a subsequent examination or investigation as in document D1 or D2 can be performed in step M4 without any reservations. If the difference in impedance $\Delta Z$ determined is more than the maximum permitted difference in impedance $\Delta Z_{MAX}$, then in a step M5 the user of the apparatus is informed by means of suitable forms of representation on the display unit 13. In the next step, M6, system parameters are changed by the workstation 12 in such a way that any heating-up of the interfering material or its surroundings that may be expected is reduced or avoided. For this purpose, reduced maximum values are, for example, given to the control unit 100 both for the magnetic fields and for the pattern followed by them over time. The control unit 10 controls the reduced currents through the pairs of coils 4 to 6 in line with the reduced field strengths preset for the magnetic fields by setting in each case the current level and a slowed waveform over time at the current amplifiers 42, 52 and 62 and the waveform generators 41, 51 and 61. Also, the field strength of the gradiented magnetic field from the pair of coils 3 is reduced by the controllable current source 31. If purposeful examination or treatment of the object is not possible even with the system set in this way, then the user can break off the examination or treatment at this point in order to remove the interfering material. For this reason, the arrow between steps M6 and M4 is shown dashed in FIG. 1.

An alternative to this is for the interfering material to be screened off from the apparatus shown in FIG. 4. For the above-mentioned examination of the neck region of the patient 1, the user of the apparatus may, once the presence of the dental filling of amalgam has been detected, screen off the neck region of the patient 1. For this purpose, a magnetic metal screening plate is positioned between the jaw region of the patient 1 and the region of action of the apparatus shown in FIG. 4. This reduces the effect of the temporally variable magnetic fields from the pairs of coils 4, 5 and 6 sufficiently for the heating-up to be reduced to an acceptable size.

Figure 2:
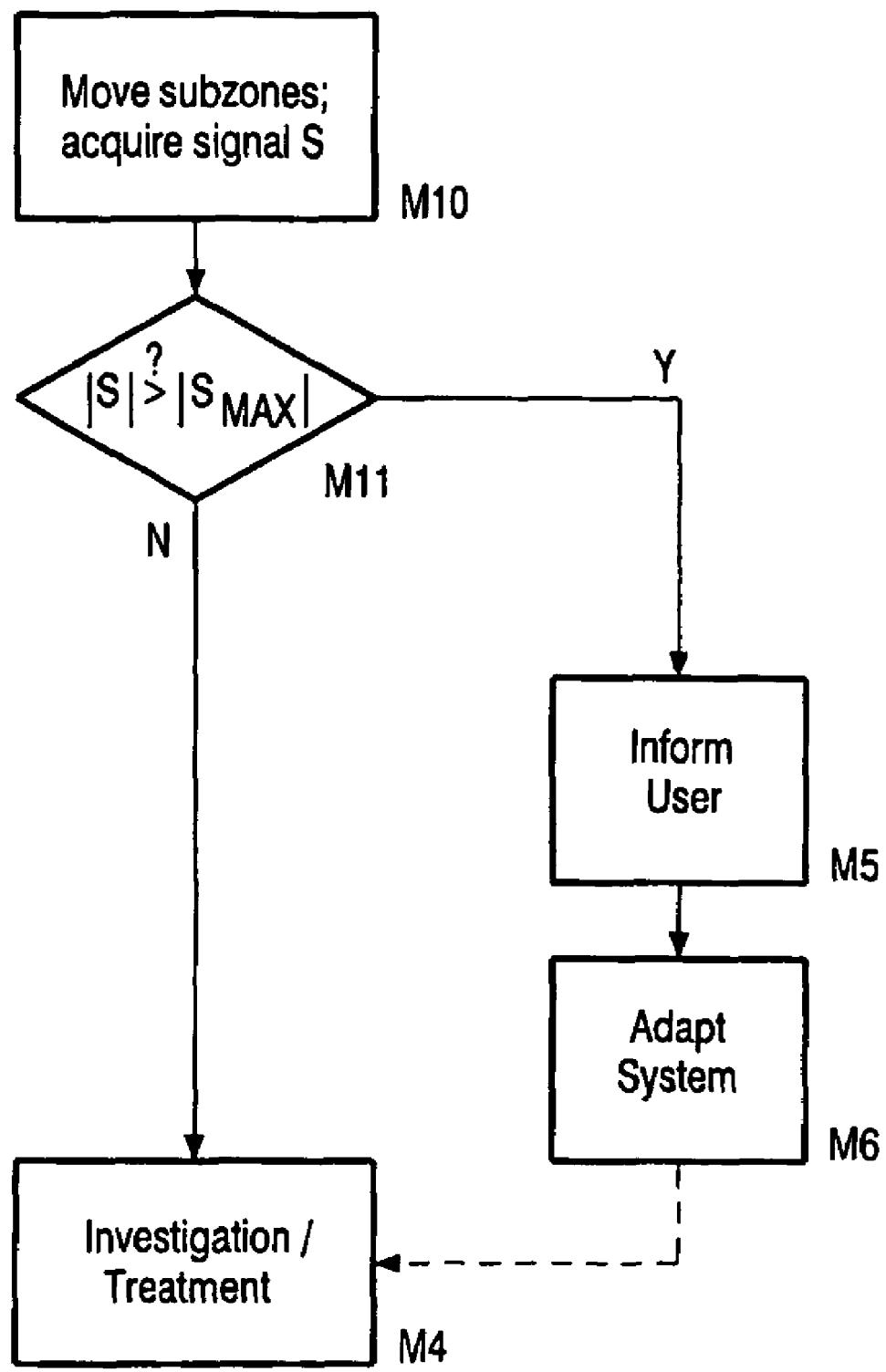
FIG. 2 is a flowchart for a second embodiment of the invention.

FIG. 2 shows the flowchart for a second embodiment of the invention. Here too, interfering material is first detected in a step M10. For this purpose, the zone 301 is moved in space, as described in documents D1 and D2, but with a reduced spatial resolution so as not to heat up the interfering material during the detection thereof. The reduction in spatial resolution can be performed in various ways:

The gradiented magnetic field from pair of coils 3 is reduced, as a result of which the spatial extent of zone 301 is enlarged.

The magnetic fields from the pairs of coils 4, 5 and 6 follow patterns over time that are such that the zone 301 passes through substantially smaller areas of the region of action than is the case at the time of an examination or treatment. This corresponds to an enlargement of the scanning grid.

In addition, the speed at which the zone 301 is moved may be reduced as well. For this purpose, the frequencies of the currents through the pairs of coils 4, 5 and 6 are reduced.

Initially, there is in the apparatus in FIG. 4 a patient to whom no magnetic particles have, as yet, been administered. If the zone 301 is now moved within the region of action, then ferromagnetic material in particular is influenced by temporally variable magnetic fields, as a result of which signals similar to those described in documents D1 and D2 for the influencing of magnetic particles are produced. These signals are thus received by the coil 7, are fed to the amplifier 72 via the filter 71, are digitized by the analog-to-digital converter 73 and are fed to the image processing unit 74. In step M11 the image processing unit 74 checks to see whether the magnitude |S| of the signals exceeds a given threshold value $|S_{MAX}|$. In this case too, the threshold value $|S_{MAX}|$ is derived from the consideration that signals (though small ones) are received even when there is, in the region of action, a patient who does not have any interfering (ferromagnetic) material. The other steps M4, M5 and M6 correspond to those in FIG. 1.

Figure 3:
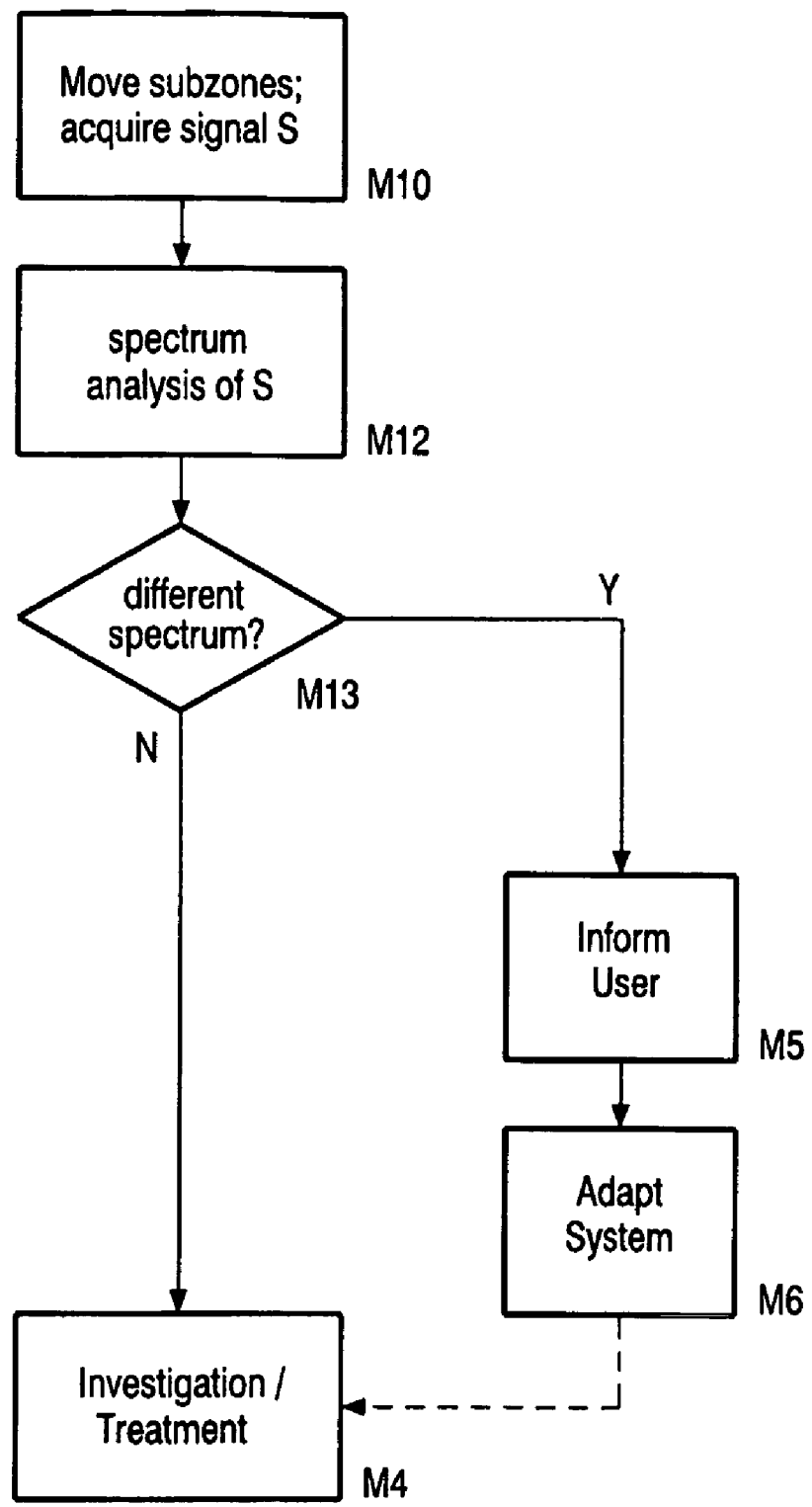
FIG. 3 is a flowchart for a third embodiment of the invention.

FIG. 3 shows the flowchart of a third embodiment of the invention. In this case magnetic particles have been administered to the patient beforehand. To allow interfering material to be detected, the first step M10, which corresponds to that in FIG. 2, is performed.

In this case too, the received signals S make their way to the image-processing unit 74 after pre-processing. The image-processing unit 74 then performs, in step M12, a frequency analysis of the signals S by breaking them down into corresponding spectral components. For the comparison that takes place in the next step, M13, the image-processing unit 74 supplies a reference spectrum that derives from signals from patients situated in the region of action who have had magnetic particles administered to them but do not have any interfering material. After any normalization that may be needed, the amounts of the individual frequency components in the signal measured are subtracted from those in the reference spectrum. When there is no interfering material present, the size of the difference is almost zero for every frequency component and step M4 can be performed. When there is interfering material present, then there are remainders at least for particular frequency components that originate from the interfering material. Steps M5 and M6 are performed in this case. Steps M4, M5 and M6 correspond to those in FIG. 1 and FIG. 2.

With the method shown in FIG. 3, it is possible for any interfering material to be detected. Ferromagnetic material, for example, behaves in a similar way to that in which it behaves in the method shown in FIG. 2 in that it generates signal components of its own. Interfering material in which eddy currents arise can be detected indirectly. With the opposing magnetic fields produced by the eddy currents, it influences surrounding magnetic particles in such a way that a change occurs in the amounts of individual spectral components in the signal measured. This change can be detected by the formation, as described above, of a difference from the reference spectrum.

The invention claimed is:

1. A method for influencing, in a region of action, magnetic particles that have been introduced into an object, the method comprising:
   a) detecting an interfering material in or on the object,
   b) generating a magnetic field having a pattern in space of its magnetic field strength such that a first sub-zone having a low magnetic field strength and a second sub-zone having a higher magnetic field strength are formed in the region of action,
   c) changing the position in space of the two sub-zones in the region of action so that the magnetization of the particles changes locally, and
   d) acquiring signals that depend on the magnetization in the region of action, which magnetization is influenced by the above change in position.

2. A method as claimed in claim 1, wherein detecting of the interfering material is performed before the magnetic particles are introduced, by measuring the change in the inductance of an inductive means that is the result of a change in the distance between the object and the inductive means.

3. A method as claimed in claim 2, wherein the inductive means comprises a coil used in the generation of the magnetic field, in the change in the position in space of the sub-zones and, where applicable, in the acquisition of the signals.

4. A method as claimed in claim 1, wherein, for the detecting, steps b) to d) are performed for a first time with a lower spatial resolution, or at a lower speed, or both, and the signals acquired are analyzed to obtain information at least on the presence of interfering material.

5. A method as claimed in claim 4, wherein the magnetic particles are not introduced into the object until after the detection.

6. A method as claimed in claim 4, wherein the magnetic particles are introduced into the object before the detection and wherein, in the analysis, the signals acquired are examined for signal components that derive from interfering material.

7. a method as claimed in claim 6, wherein interfering material is detected from the spectral composition of the signals acquired.

8. A method as claimed in claim 1, wherein, if interfering material is present, magnetic fields having a reduced temporal variation are used during the influencing of the magnetic particles to change the position in space of the two sub-zones.

9. A method as claimed in claim 1, wherein, if interfering material is present, steps b) and c) are performed with a reduced spatial resolution during the influencing of the magnetic particles.

10. An arrangement for influencing magnetic particles in a region of action, comprising:
    a) means for detecting interfering material,
    b) means for generating a magnetic field having a pattern in space of its magnetic field strength such that a first sub-zone having a low magnetic field strength and a second sub-zone having a higher magnetic field strength are formed in the region of action,
    c) means for changing the position in space of the two sub-zones in the region of action, and
    d) means for acquiring signals, which signals depend on the magnetization in the region of action that is influenced by the change in the position in space of the sub-zones.

11. An arrangement as claimed in claim 10, further comprising means for measuring the inductance of at least one of an inductive means that are used for the generation of the magnetic field, for the change in the position in space of the sub-zones and/or for the acquisition of the signals.

12. An arrangement as claimed in claim 10 further comprising an analyzing unit to obtain information on at least the presence of interfering material.

13. An arrangement as claimed in claim 12, wherein the analyzing unit is adapted to examine the signals acquired for signal components deriving from magnetic particles and also from interfering material.

* * * * *